United States Patent [19]

Becker et al.

[11] Patent Number: 5,600,018
[45] Date of Patent: Feb. 4, 1997

[54] PREPARATION OF GLUTARALDEHYDE

[75] Inventors: Rainer Becker, Bad Dürkheim; Wolfgang Friedrich, Speyer; Walter Klink, Birkenheide; Juergen Schossig, Fussgönheim; Andreas Henne, Neustadt, all of Germany

[73] Assignee: BASF Aktiengesellschaft, Ludwigshafen, Germany

[21] Appl. No.: 512,151

[22] Filed: Aug. 7, 1995

[30]  Foreign Application Priority Data

Aug. 18, 1994 [DE] Germany ............... 44 29 262.7

[51] Int. Cl.⁶ .............. C07C 47/12; C07C 45/60
[52] U.S. Cl. ................................................. 568/483
[58] Field of Search ...................................... 568/483

[56]  References Cited

U.S. PATENT DOCUMENTS

| | | |
|---|---|---|
| 2,546,018 | 3/1951 | Smith et al. ............. 568/483 |
| 4,244,876 | 1/1981 | Warner et al. ............ 568/421 |
| 4,448,977 | 5/1984 | Warner et al. ............ 568/483 |

FOREIGN PATENT DOCUMENTS 66224  12/1982  European Pat. Off. .

OTHER PUBLICATIONS

Thuy et al, Bull. Soc. Chim. Fr., vol. 79 (1978), pp. 264–265.
JP 72 27 488, Glutaraldehyde continuous prepn, Sumitomo Chemical Co., Ltd., (1967), Abstract.

*Primary Examiner*—Joseph K. McKane
*Assistant Examiner*—Laura L. Stockton
*Attorney, Agent, or Firm*—John H. Shurtleff

[57]  ABSTRACT

A process for preparing glutaraldehyde by reaction of alkoxydihydropyrans of the general formula I

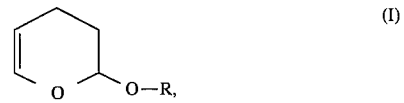

(I)

where R is $C_1$–$C_{20}$-alkoxy, with water at from 0° to 150° C. and from 0.01 to 50 bar in the presence of a catalyst consisting essentially of a bleaching earth.

9 Claims, No Drawings

PREPARATION OF GLUTARALDEHYDE

The present invention relates to a process for preparing glutaraldehyde by reaction of alkoxydihydropyrans with water in the presence of bleaching earths as catalyst.

U.S. Pat. No. 2,546,018 discloses the thermal hydrolysis of alkoxydihydropyrans at from 100° to 200° C. to give glutaraldehyde. To reduce the reaction temperature acidic catalysts are proposed.

Homogeneous acid catalysis using e.g. $H_3PO_4$ is disclosed in JP 72 26 488. The uses described here of homogeneous acids as catalysts for the hydrolysis of alkoxypyran to glutaraldehyde have the disadvantage that the acids remain in the system after reaction is complete and therefore have to be neutralized. In this form, they cause discolorations of the glutaraldehyde or they catalyze the polymerization of glutaraldehyde and thus cause undesirable turbidity due to deposition of polymer. The tendency of glutaraldehyde to polymerize is known and is in general largely suppressed by handling in dilute aqueous solution. On account of these problems, various processes have been described, inter alia using acidic ion exchangers as hydrolysis catalysts (EP-A-66 224, U.S. Pat. Nos. 4,244,876 and 4,448,977). These processes describe the reaction of alkoxydihydropyrans with water or alcohol to give hydroxyalkoxytetrahydropyran or to give dialkoxytetrahydropyran as a stable glutaraldehyde precursor. The reaction to give the desired glutaraldehyde must thus be additionally carried out subsequently. Besides this disadvantage, inadequate catalyst activity or service life and the high price of the ion exchangers are unsatisfactory here.

It is an object of the present invention to remedy the above-mentioned disadvantages.

We have found that this object is achieved by a novel and improved process for preparing glutaraldehyde by reaction of alkoxydihydropyrans of the general formula I

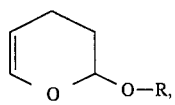
(I)

where R is $C_1$–$C_{20}$-alkyl, with water at from 0° to 150° C. and from 0.01 to 50 bar in the presence of a catalyst, which comprises employing bleaching earths as catalyst.

The process according to the invention can be carried out as follows:

The alkoxydihydropyran I and water can be reacted at from 0° to 150° C., preferably 30° to 100° C., particularly preferably 40° to 80° C., and from 0.01 to 50 bar, preferably 0.1 to 5 bar, particularly preferably at atmospheric pressure (normal pressure), in the presence of bleaching earths as catalyst to give glutaraldehyde.

Suitable bleaching earth catalysts are, for example, aluminum hydrosilicates or aluminum magnesium hydrosilicates of the montmorillonite type, which can be activated e.g. by acids and are commercially available, for example, under the name Tonsil (e.g. Südchemie). As is known, bleaching earths are used in industry, inter alia as acidic catalysts in the alkylation of phenols or aromatic amines. Their catalytic action in the preparation of glutaraldehyde was unknown until now.

It ensues from the abovementioned prior art that 2-hydroxy-6-alkoxytetrahydropyrans are passed through as intermediates. These intermediates can be analytically detected or even isolated, depending on the excess of water.

As a rule, the molar ratio of water to the alkoxydihydropyran I is from 1:1 to 100:1, preferably 1:1 to 20:1, particularly preferably 1:1 to 10:1.

The substituent R in the compounds I has the following meanings:

$C_1$–$C_{20}$-alkyl, preferably $C_1$–$C_8$-alkyl, particularly preferably $C_1$–$C_4$-alkyl such as methyl, ethyl, n-propyl, isopropyl, n-butyl, isobutyl, sec-butyl, or tert-butyl, in particular methyl and ethyl.

Suitable alkoxydihydropyrans I are preferably 2-alkoxy-3,4-dihydropyrans such as 2-methoxy-3,4-dihydropyran, 2-ethoxy-3,4-dihydropyran, 2-n-propoxy-3,4-dihydropyran, 2-isopropoxy-3,4-dihydropyran, 2-n-butoxy-3,4-dihydropyran, 2-isobutoxy-3,4-dihydropyran, 2-sec-butoxy-3,4-dihydropyran and 2-tert-butoxy-3,4-dihydropyran, particularly preferably 2-methoxy-3,4-dihydropyran and 2-ethoxy-3,4-dihydropyran.

Glutaraldehyde is used e.g. in tanning or as a microbicide.

EXAMPLES

Example 1

Batchwise procedure 114 g of methoxydihydropyran (1 mol) are stirred at 50° C. in a 3-necked flask with 57 g of water (3.2 mol) and 5 g of catalyst KSF (supplied by Südchemie). After 90 min the conversion is approximately 70%, and after 5 hours >99% (gas-chromatographic checking). After 5 hours the mixture is cooled and the catalyst is separated off; according to GC the crude mixture contains <0.1% starting material and 73% glutaraldehyde. After distilling off the eliminated methanol the glutaraldehyde content is >90% (calc. as anhydrous).

Example 2

Continuous procedure

Methoxydihydropyran is hydrolyzed to glutaraldehyde in a tubular reactor packed with 1.2 l of catalyst strands (K10 from Südchemie) by continuous supply of 40 ml/h of methoxydihydropyran (0.36 mol) and 20 ml/h of water (1.1 mol) at 70° C. and recycling of 12 l/h of reaction solution. The material discharged from the reactor is single-phase and clear, the composition according to GC is unchanged over a running time of 20 days and is, after distilling off the methanol, <1% methoxydihydropyran and 85–90% glutaraldehyde.

We claim:

1. A process for preparing glutaraldehye which comprises: reacting an alkoxydihydropyran of the formula I

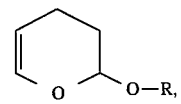
(I)

wherein R is $C_1$- to $C_{20}$-alkyl, with water at from 0° to 150° C. and from 0.01 to 50 bar in the presence of a catalyst consisting essentially of a bleaching earth.

2. A process as claimed in claim 1, wherein R in the formula I is $C_1$- to $C_8$-alkyl.

3. A process as claimed in claim 1, wherein R in the formula I is $C_1$- to $C_4$-alkyl.

4. A process as claimed in claim 1, wherein R in the formula I is methyl or ethyl.

5. A process as claimed in claim 1, wherein the reaction is carried out at a temperature of from 30° to 100° C.

6. A process as claimed in claim 1, wherein the reaction is carried out at a pressure of from 0.1 to 5 bar.

7. A process as claimed in claim 1, wherein the reaction is carried out at atmospheric pressure.

8. A process as claimed in claim 1, wherein the molar ratio of water to the alkoxydihydropyran I is from 1:1 to 20:1.

9. A process as claimed in claim 1, wherein the molar ratio of water to the alkoxydihydropyran I is from 1:1 to 10:1.

* * * * *

UNITED STATES PATENT AND TRADEMARK OFFICE
CERTIFICATE OF CORRECTION

PATENT NO. : 5,600,018
DATED : Feb. 4, 1997
INVENTOR(S) : Becker et al

It is certified that error appears in the above-indentified patent and that said Letters Patent is hereby corrected as shown below:

In the Abstract at line 3 from the bottom, cancel: "$C_1$-$C_{20}$-alkoxy", and substitute -- $C_1$-$C_{20}$-alkyl --.

Signed and Sealed this

Twelfth Day of August, 1997

*Attest:*

BRUCE LEHMAN

*Attesting Officer*  *Commissioner of Patents and Trademarks*